United States Patent [19]
Togawa

[11] 4,090,513
[45] May 23, 1978

[54] HEAT AND MOISTURE EXCHANGING DEVICE FOR RESPIRATION

[75] Inventor: Tatsuo Togawa, Funabashi, Japan
[73] Assignee: Termuo Corporation, Tokyo, Japan
[21] Appl. No.: 667,988
[22] Filed: Mar. 18, 1976
[30] Foreign Application Priority Data
  Mar. 20, 1975 Japan .................. 50-37858[U]
[51] Int. Cl.² ............................. A61M 16/00
[52] U.S. Cl. .................. 128/212; 128/351;
      55/DIG. 35; 55/466; 73/715
[58] Field of Search ............ 128/212, 186, 187, 188,
      128/191 R, 192, 202, 203, 142, 142.2, 142.6,
      146.2, 146.6, 147, 2.05 D, 2.05 E, 2.05 F, 2.05
      V, DIG. 29, DIG. 17, 145.5, 145.8, 351;
      73/406, 407 R, 407 PR, 398 C

[56] References Cited

U.S. PATENT DOCUMENTS

| | | | |
|---|---|---|---|
| 2,610,038 | 9/1952 | Phillips | 128/202 |
| 2,997,131 | 8/1961 | Fisher | 55/466 |
| 3,611,178 | 10/1971 | McConnell | 128/DIG. 17 |
| 3,747,598 | 7/1973 | Cowans | 128/147 |
| 3,911,899 | 10/1975 | Hattes | 128/145.8 |
| 3,965,746 | 6/1976 | Rabek | 73/398 C |
| 4,018,580 | 4/1977 | Burkholz et al. | 55/321 |

FOREIGN PATENT DOCUMENTS

| | | | |
|---|---|---|---|
| 85,055 | 8/1954 | Denmark | 128/212 |
| 2,223,474 | 11/1973 | Germany | 128/212 |
| 1,086,806 | 10/1967 | United Kingdom | 128/212 |

*Primary Examiner*—Robert W. Michell
*Assistant Examiner*—Henry J. Recla
*Attorney, Agent, or Firm*—Carroll F. Palmer

[57] ABSTRACT

A heat and moisture exchanging device for respiration comprising a housing, having an inlet detachably connected to a tracheal cannula and an outlet detachably connected to a tube for passing respiratory air, and a permeable heat and moisture exchange body provided between said inlet and outlet. The device can indicate the respiration state of a patient by including an air pressure differential monitor operating across said outlet and inlet to detect the number of breaths per unit time, respired air volume and volume of tidal air.

4 Claims, 12 Drawing Figures

HEAT AND MOISTURE EXCHANGING DEVICE FOR RESPIRATION

BACKGROUND OF THE INVENTION

This invention relates to a heat and moisture exchanging device for respiration suitable for conducting general anesthesia, artificial respiration, etc. The device according to this invention is capable of adjusting appropriately the physical conditions of the inhaling air and, at the said time, observing the number of breaths per unit time, respired air volume and the volume of tidal air.

Where general anesthesia or artificial respiration is applied to a patient, one end of the tracheal cannula is inserted into the trachea and the other end connected to an anesthetizing device or a respirator. In this case, the mucous membrane of the upper portion of the respiratory tract loses its physiologial air conditioning function which would be performed in normal respirations. Namely, in normal respirations, heat and moisture of the exhaling air are absorbed by the inner walls of nasal cavities, oral cavity and pharynx and a major part of the heat and moisture thus absorbed is imparted to the inhaling air so as to make it suitable for inhalation.

However, where a tracheal cannula is inserted into the trachea for respirations, the exhaling air comes out of the human body hot and humid and the inhaling air is scarcely warmed nor moistened, because the inner wall of the cannula is smooth and, thus, inferior in capabilities of moisture absorption and heat exchange. It follows that the application of an anesthetizing device or a respirator for a long time causes the respiratory tract of the patient to be dried, giving the patient hard pains. In some cases, lung diseases are possibly caused.

To solve the problem, conventional devices for general anesthesia or artificial respiration utilize moistening means such as nebulizer so as to moisten the inhaling air appropriately. But, where, for example, a nebulizer is used in an anesthetizing device of a closed circulation type, it is undesirable to add excessive moisture to the inhaling air because the carbon dioxide absorbing agent used in the anesthetizing device is hygroscopic in nature. When used in a respirator, it is difficult for the nebulizer always to impart appropriate moisture to the inhaling air.

Also known is a device using aluminum foils for recovering the moisture and heat of the exhaling air (see Acta anaesth, Scandinav. 1960, 4, pages 105–124, "POSTOPERATIVE CARE AND COMPLICATIONS AFTER TRACHEOTOMY IN INFANTS AND CHILDREN"). This device, however, fails to give a satisfactorily sharp temperature gradient across the heat exchange body. Thus, a large dead space is required for sufficiently recovering moisture and heat from the exhaling air.

It should also be noted that, where a tracheal cannula is used for conducting a medical operation or applied to a patient with an advanced disease, it is necessary to check the number of breaths per unit time, respired air volume and the volume of tidal air besides the warming and moistening problems described. For observation of the number of breaths per unit time, known is a method in which is used a thermistor placed inside the nasal cavities or mounted at the outer end of a tracheal cannula. In this case, the number of breaths is measured from the temperature changes of the respiratory air detected by the thermistor. This method, however, fails to measure the volume of tidal air. Hot wire anemometers or the like are available for the measurement of the volume of tidal air. But, any of conventional devices is unsuitable for services for a long time. Particularly, inconveniences in sterilization are a nuisance.

SUMMARY OF THE INVENTION

This invention has been achieved to remove the above-mentioned drawbacks. Specifically, an object of this invention is to provide a heat and moisture exchanging device for respiration small in dead space and total size, simple in structure and capable of performing air conditioning functions comparable to those performed by physiological air conditioning mechanism during normal respirations.

Another object is to provide a device equipped with a mechanism capable of observing the number of breaths per unit time and the volume of tidal air.

More in detail, the heat and moisture exchanging device for respiration according to this invention comprises a tubular housing having an inlet detachably connected to a tracheal cannula and an outlet detachably connected to a tube for passing respiratory air. Provided between these inlet and outlet are a plurality of permeable heat and moisture exchange layers arranged substantially perpendicular to the respiratory air passage. Moisture and heat of the exhaling air are absorbed by these layers and, then, imparted to the inhaling air.

The air adjusting device of this invention further comprises a mechanism communicated with the inlet and outlet of the housing by means of a pair of tubes, said mechanism serving to detect the air pressure difference between the inlet and outlet, thereby measuring the number of breaths per unit time and the volume of tidal air.

DETAILED DESCRIPTION OF THE PREFERRED EMBODIMENTS

Figure 1:
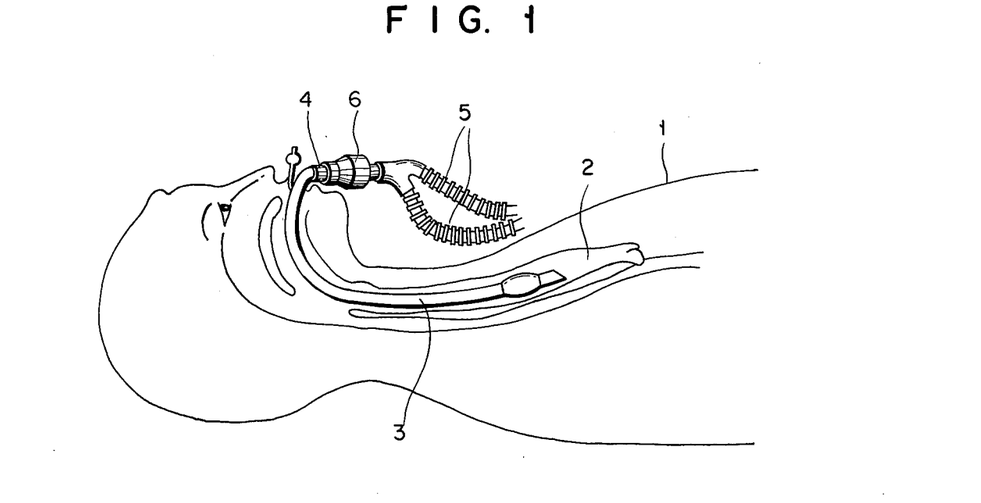
FIG. 1 illustrates a condition under which is used the heat and moisture exchange device for respiration according to this invention.

FIG. 1 shows a condition in which a tracheal cannula 3 is inserted into the trachea 2 of a patient 1. A junction portion 4 is provided at the exterior end of the tracheal cannula 3. In a conventional device for conducting general anesthesia or artificial respiration, it is customary to connect a single or a plurality of hoses 5, which communicate with an anesthetizing device or a respirator, directly to the junction portion 4. In the present invention, however, a heat and moisture exchanging device 6 is provided between the junction portion 4 and the hose 5.

Figure 2:
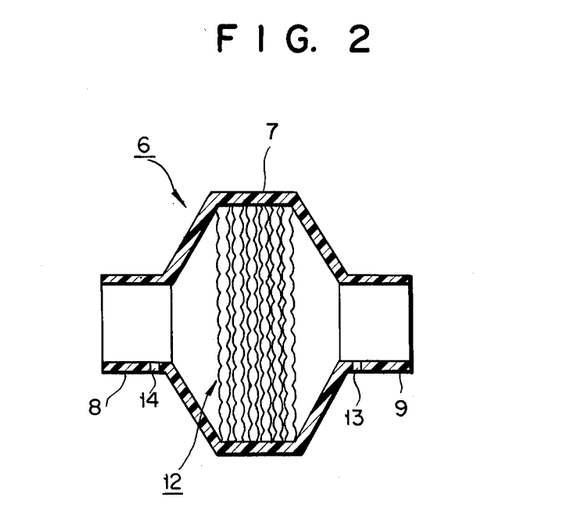
FIG. 2 is a cross sectional view of a device according to one embodiment of this invention.
Figure 3:
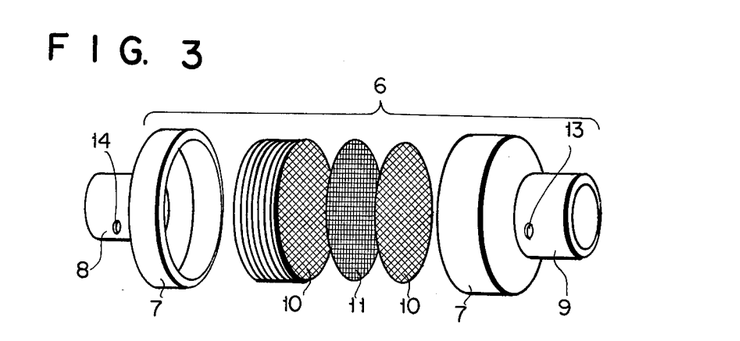
FIG. 3 is an exploded view showing the assemblage of parts of the device shown in FIG. 2.

As shown in FIG. 2, the heat and moisture exchaning device according to this invention comprises a housing consisting of an enlarged central portion 7 and an inlet 8 and an outlet 9 provided on each side of the central portion 7. Housed in the central portion 7 is a heat and moisture exchange body 12 consisting of moisture absorptive heat-insulating sheets 10 and permeable heat-conductive sheets 11. For example, the heat-insulating sheets 10 and the heat-conductive sheets 11 are alternately superposed to form the heat and moisture exchange body 12. The heat-insulating sheet 10, disk-like in shape, is made of, for example, gauze or non-woven fabric. On the other hand, the heat-conductive sheet 11, also disk-like in shape, is made of a mesh of metal such as aluminum. The tracheal cannula 3 and the hose 5 are detachably connected to the inlet 8 and the outlet 9, of the housing, respectively. Further, tube insertion holes 13 and 14 are provided on the walls of the inlet 8 and the outlet 9. As described later, a differential pressure gauge is communicated with the air adjusting device through these holes 13 and 14.

It is recommended to prepare the heat and moisture exchange body 12 with the age, weight, etc. of the patient fully taken into account. For example, it is preferred to superpose alternately several or scores of the moisture absorptive heat-insulating sheets 10 and the heat conductive sheets 11, each sheet being 30 to 50 mm in diameter. The moisture absorptive heat-insulating sheet 10 is advantageous in that it enables the heat exchange body 12 to exhibit an increased heat insulation effect, a sharpened temperature gradient across it, a good moisture recovery from the exhaling air, etc. But, the heat-insulating sheets 10 may be omitted, allowing the heat exchange body 12 to be formed of the heat conductive sheets alone.

It is important that the sheets constituting the heat exchange body be disposed substantially perpendicular to the passage of the respiration air. Unlike the case where the sheets are arranged parallel with the air passage, the sheets arranged perpendicular to the air passage are advantageous because an air layer acting as a heat insulating layer is formed between every two adjacent sheets. The heat insulating layers thus formed serve to sharpen the temperature gradient across the heat exchange body. It follows that heat and moisture are effectively recovered from the exhaling air with a thinner heat and moisture exchange body. In addition, it is possible to decrease the amount of water condensed from the vapor of the exhaling air within the heat and moisture exchanging device.

Sheets having appropriate sizes of mesh for example about 14 meshes (about 1.2 mm), can be used for preparing the heat exchange body 12.

When the heat and moisture exchanging device 6 mounted between the tracheal cannula 3 and the hose 5 is applied to a patient, the exhaling and inhaling airs alternately pass through the heat and moisture exchanging device in opposite directions. When the exhaling air, having about 100% of relative humidity in coming out of the lung, passes through the heat exchange body 12 of the heat and moisture exchanging device 6, it is cooled and condensed so as to form fine water drops on the surface of the heat exchange body 12, with the latent heat given to the heat exchange body 12. On the other hand, the inhaling air is warmed in passing through the heat exchange body 12 and moistened by the water vaporized within the heat and moisture exchaning device. By the process described, the heat and moisture of the exhaling air are recovered by the inhaling air.

Figure 7:
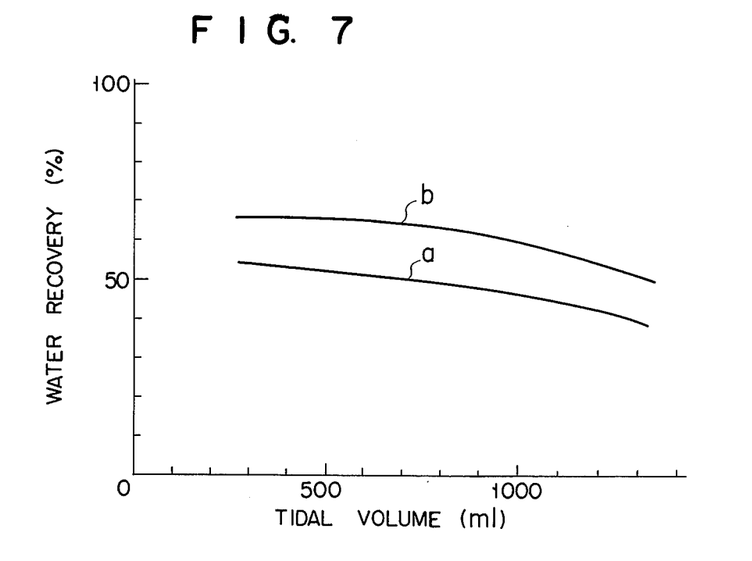
FIGS. 7 and 8 respectively show the performances of the devices according to this invention.
Figure 8:
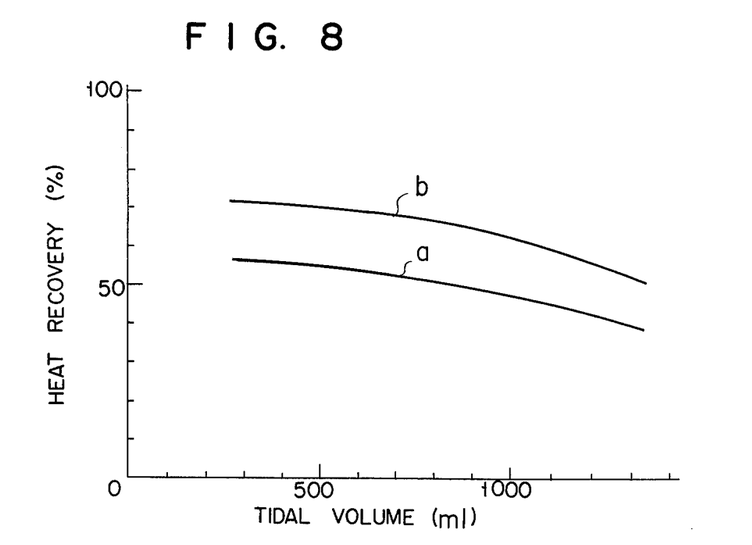

FIGS. 7 and 8 respectively show the experimental results of the recovering effects of moisture (water) and heat of the heat and moisture exchanging device. In these drawings, the curve (a) represents the case where the heat exchange body was formed of ten pieces of aluminum mesh, the mesh size being about 1.5 mm, the total weight of the heat and moisture exchange body being 2.5g, and the dead space of the heat exchange body being 10.5 ml. In this case, the heat and moisture exchanging device was applied to an artificial respiration under the conditions of the air stream resistance 0.8 cm $H_2O/l/sec.$, the ambient temperature 24° C, and the relative humidity of the atmosphere 30%. The curve (b) represents the case where the heat and moisture exchange body was prepared by inserting gauze (mesh size being about 1 mm) into the spaces between two adjacent aluminum meshes of the heat exchange body used for the case of the curve (a). Thus, the dead space of the heat and moisture exchange body was 10.5 ml as in curve (a). In this case, the heat and moisture exchanging device was applied to an artificial respiration under the air stream resistance of 1.2 cm $H_2O/l/sec.$, the other conditions being the same as in curve (a).

These graphs show that the heat and moisture exchanging device of this invention is capable of recovering about 40 to 70% of moisture and heat, the values being comparable to those in normal respirations. Particularly, the recovering effects for the curve (b) are prominent. In this case, the gauze serves to improve the functions of the heat and moisture exchange body. In addition, the moisture absorbed by the gauze renders the heat capacity far greater than that of the aluminum mesh. These combine to permit decreasing markedly the dead space of the heat exchange body. Incidentally, the air stream resistance can be adjusted appropriately by suitably selecting the mesh size, diameter, etc. of the sheets constituting the heat and moisture exchange body.

Figure 4:
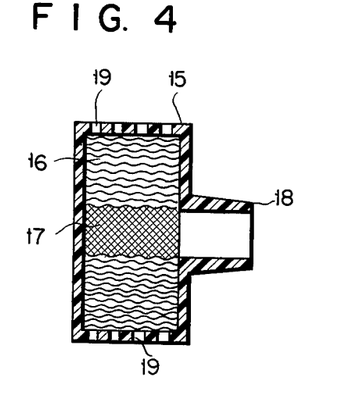
FIG. 4 is a cross sectional view of a heat and moisture exchanging device according to another embodiment of this invention.
Figure 5:
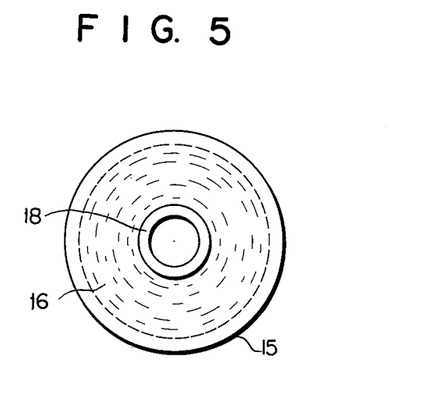
FIG. 5 is a plan view of the device shown in FIG. 4.

FIGS. 4 and 5 collectively show a heat and moisture exchanging device according to another embodiment of this invention. The device shown is suitable for use in the case where a respirator or the like is not required. The tracheal cannula 3 or the incised respiratory track is connected to the device. It is seen that a cylinder 15 closed at one end houses a heat and moisture exchange body 16 formed by spirally winding a band-like aluminum mesh singly or together with gauze so as to form a central free space 17. The open end of the cylinder 15 is communicated with an inlet 18 to which is connected the tracheal cannula. A number of air passages 19 are formed on the wall of the cylinder 15 so as to permit respirations through the inlet 18. Simple construction is one of the merits of the device of this type. Further, it is easier to manufacture the heat and moisture exchange body 16. Moreover, the device described permits decreasing the dead space.

Figure 6:
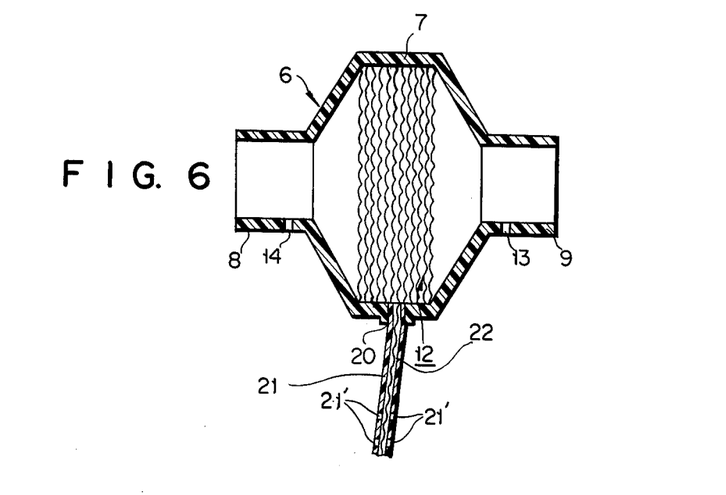
FIG. 6 is a cross sectional view of a heat and moisture exchanging device according to still another embodiment of this invention.

FIG. 6 shows a heat and moisture exchanging device according to still another embodiment of this invention. In this case, a drainage hole 20 is provided on the bottom of the wide central portion 7 of the heat and moisture exchanging device shown in FIG. 2. A drainage tube 21 having a plurality of side openings 21′ and loaded with a fibrous material 22 such as gauze or string is connected to the drainage hole 20. The device of this type is effective when used such a long time that water condensed from vapor unavoidably accumulates to some extent on the bottom of the central portion 7. In such a case, the accumulated water should be removed by the capillary action of the fibrous material 22 housed in the drainage tube 21 in order to avoid inaccuracy in data due to an increased fluid resistance when a differential pressure gauge is employed as described below.

Figure 9:
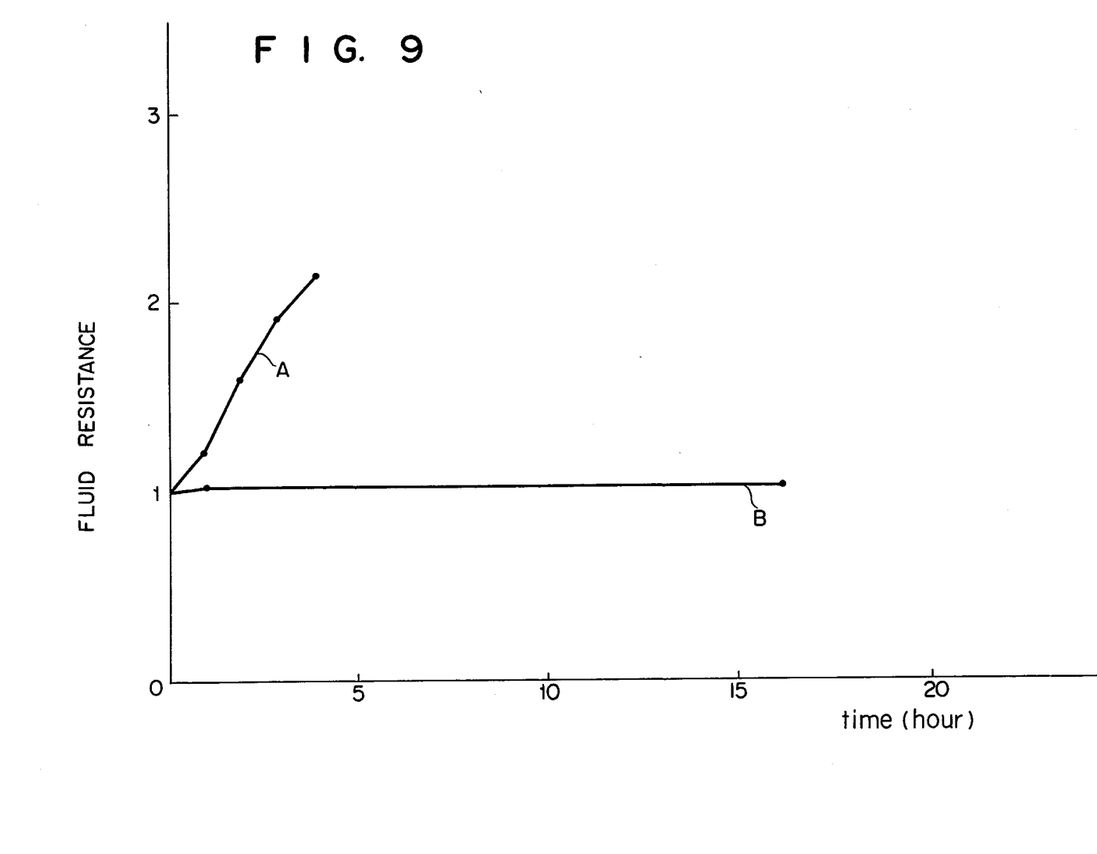
FIG. 9 shows changes with time in fluid resistance.

FIG. 9 shows changes with time in air flow resistance (fluid resistance) of heat and moisture exchanging devices according to this invention. Curve A represents the case where the heat exchange body prepared by alternately superposing eleven aluminum sheets and ten pieces of gauze was housed in such a heat and moisture exchanging device as shown in FIG. 2. The diameter of the central portion of the device was 30 mm. Curve B denotes the case where a heat and moisture exchanging device similar to that for curve A was provided with a drainage tube 40 cm long and 3 mm in inner diameter as shown in FIG. 6. The experiments were conducted under the conditions of the ambient temperature 25° C, the relative humidity of the atmosphere 70%, the tidal volume 513 ml, the exhaling air temperature 37° C and the respiration period 4.2 seconds. It is seen that the fluid resistance for curve A increased to more than twice the value for curve B, where a drainage tube was provided, four hours after the experiments began. Further, the change in fluid resistance for curve B was negligible more than 15 hours later.

Figure 10:
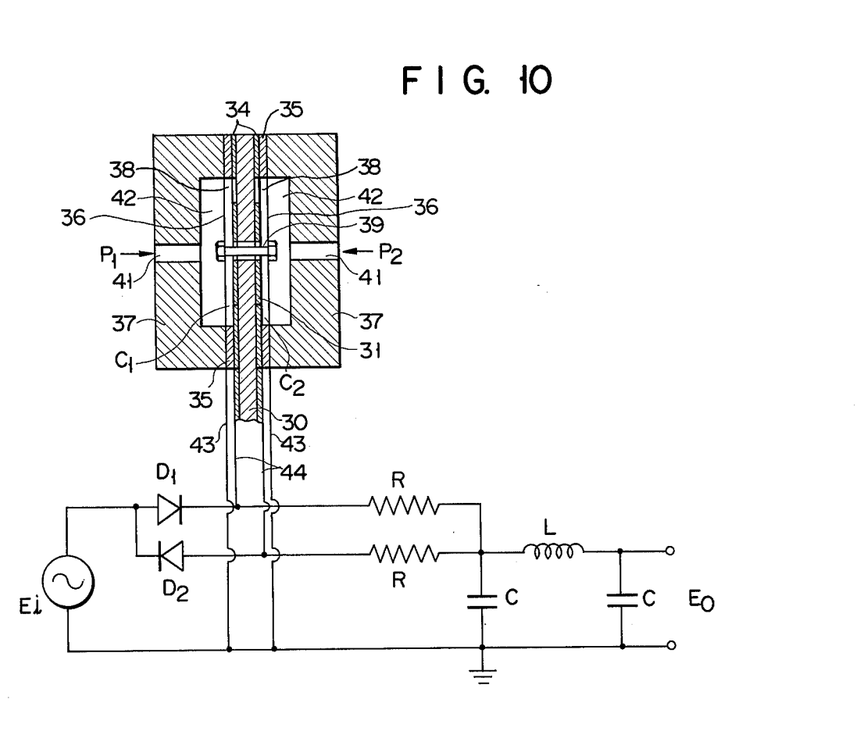
FIG. 10 shows a cross section of a device according to one embodiment of this invention for detecting the air pressure difference between the inlet and outlet, said device being used in the air conditioning device shown in FIG. 2. The electric circuit concerned is also shown in FIG. 10.
Figure 11:
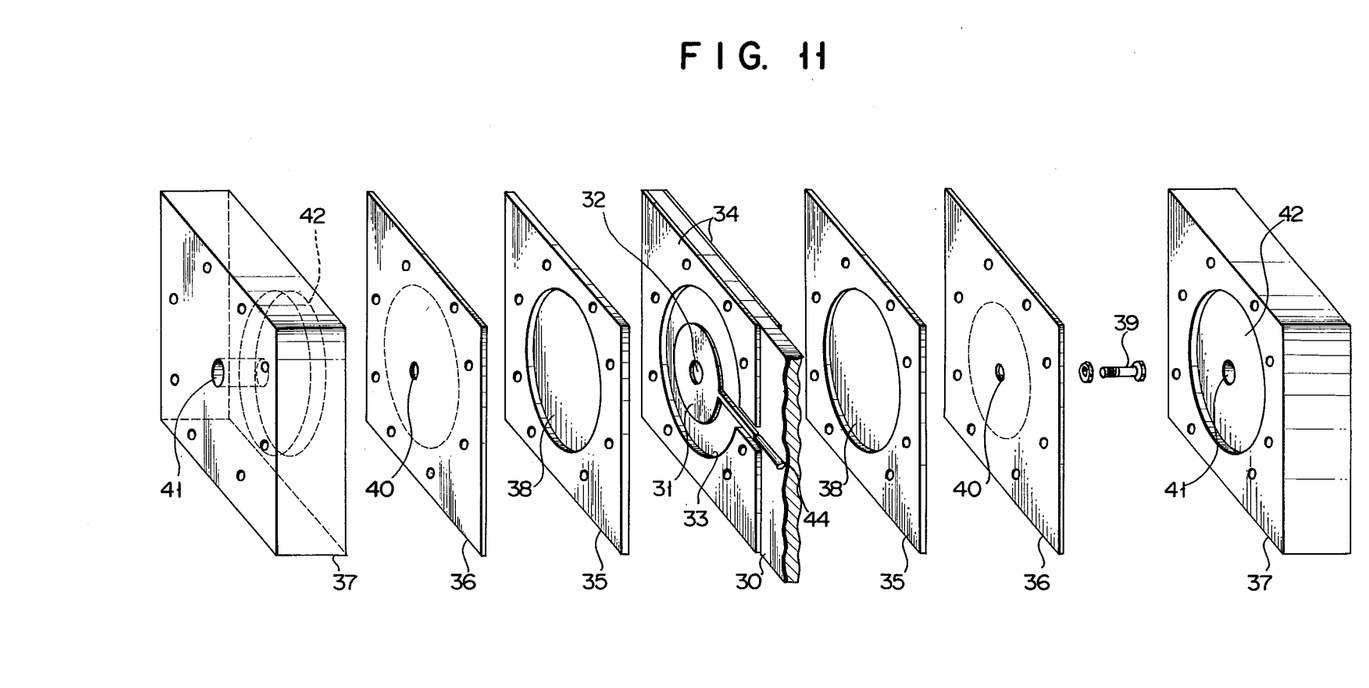
FIG. 11 is an exploded view of the device shown in FIG. 10.

In the heat and moisture exchanging device 6 shown in FIG. 2, housed is the heat and moisture exchange body 12 as described previously. Thus, owing to the air stream resistance, a pressure drop is caused between the inlet 8 and the outlet 9 in proportion to the flow of the respiration air. The pressure difference or the pressure drop, can be measured by communicating the inlet and outlet with a differential pressure gauge by means of tubes. Specifically, one end of a tube is connected to the hole 13 provided on the wall of the outlet 9, and the other end to the differential pressure gauge. Likewise, one end of another tube is connected to the hole 14 provided on the wall of the inlet 8, the other end being connected to the differential pressure gauge. FIGS. 10 and 11 collectively show an example of the differential pressure gauge, which detects the pressure difference utilizing the variations of the capacitances of the condensers formed therein.

As shown in FIG. 11, annular electrodes 31 are respectively fixed to each surface of a substrate 30. These electrodes 31 are arranged to be concentric with a through-hole 32 bored at the center of the substrate 30. Further, metal plates 34 having the same thickness as the annular electrodes 31 are respectively fixed to each side of the substrate 30 in a manner of forming annular clearances 33 between the electrodes 31 and the metal plates 34. In this case, the clearances 33 are concentric with the annular electrodes 31. An insulating spacer 35, a diaphragm 36, and a lid 37 are laminated in the order mentioned on each side of the substrate 30. In the central portion of the insulating spacer 35 is formed an opening 38 whose periphery substantially conforms to the outer periphery of the annular clearance 33.

The diaphragm 36 is made, for example, of a stainless steed plate 0.1 mm thick. It should be noted that the air stream resistance across the heat exchange body 12 should not be a burden on the respiratory action. The value is about 14 cm $H_2O/l$/sec. and, the pressure difference between the inlet 8 and the outlet 9 is less than 1 cm $H_2O$ at most. It follows that the diaphragm 36 should be so flexible as to respond readily to such a small pressure difference. A threaded hole 40 is provided at the center of each of the diaphragm 36 and as shown in FIG. 10, the two diaphragms 36 are tightened by a screw rod 39.

It should be noted that two condensers (or capaciters) are formed inside the assembly, each consisting of one diaphragm (stainless steel) and one electrode. Namely, one condenser is formed each on the inlet and outlet sides.

Provided at the center of the lid 37 is a hole 41 for receiving one end of the tube leading to the heat and moisture exchanging device 6. Also provided is a circular depression 42 whose periphery corresponds to the outer periphery of the clearance 33 between the electrode 31 and the metal plate 34 fixed to the substrate 30.

The diaphragms 36 and the electrodes 31 are respectively connected to the electric circuit by lead wires 43 and other lead wires 44 as shown in FIG. 10 so as to form two condensers (capacitors).

The electric circuit shown in FIG. 10 denotes one example of the construction of a differential pressure gauge. In this case, the condenser formed on the inlet side having the capacitance $C_1$ and the condenser formed on the outlet side having the capacitance $C_2$ jointly form a smoothing condenser for the rectifying circuit shown. Quite naturally, $C_1$ and $C_2$ vary depending on the pressure difference between the inlet 8 and the outlet 9 of the heat and moisture exchanging device.

As described previously, the two diaphragms 36 are joined and fixed by the rod 39. In this case, the hole 32 through the substrate 30 leaves a free space. It follows that when pressure $P_1$ on the inlet side is higher than $P_2$ on the outlet side, the diaphragm 38 shown in FIG. 10 is pushed toward the annular electrode 31, decreasing the distance between the plate 36 and the electrode 31. Namely, the capacitors $C_1$ is increased. Under the state described, the diaphragm on the outlet side is pushed outward so as to increase the distance between the two metal plates forming the condenser on the outlet side. Thus, the capacitance $C_2$ is decreased.

FIG. 10 shows a circuit comprising a crystal oscillator Ei, silicon diodes $D_1$, $D_2$, resistors R, R, condensers C, C and a coil L. It is seen that a $\pi$-type smoothing circuit is formed by the condensers C, C and the coil L. The alternating voltage generated by the crystal oscillator Ei is recitified by the diode $D_1$, the condenser of capacitance $C_1$, the diode $D_2$, the condenser of capacitance $C_2$ and then, smoothed by the $\pi$-type LC circuit so as to generate an output voltage Eo between the output terminals. It should be noted that when there is a difference between $P_1$ and $P_2$ a difference is generated between $C_1$ and $C_2$ and the output voltage Eo becomes not equal to zero. Namely, Eo depends on the differnce between C1 and C2.

Figure 12:
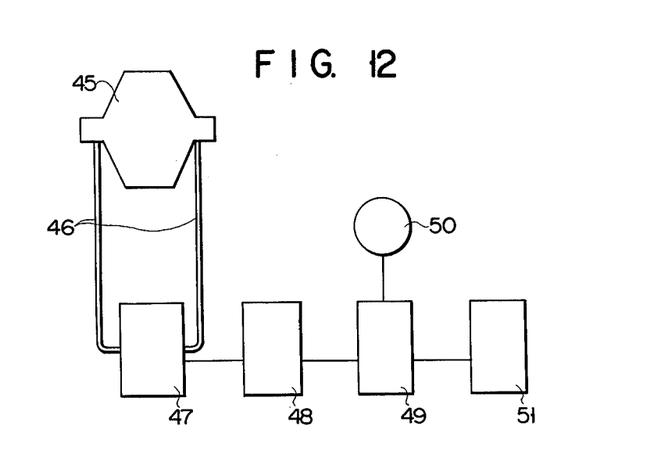
FIG. 12 is a block diagram for explaining the observation system of the number of breaths per unit time and the volume of tidal air, said system being incorporated into the heat and moisture exchanging device for respiration.

The output voltage Eo is applied to a respiration observation system as shown in FIG. 12. It is seen that the inlet and outlet of a heat and moisture exchanging device 45 are communicated with a differential pressure gauge 47 by means of a pair of tubes 46, so as to enable the gauge 47 to receive the pressures inside the inlet and the outlet. The differential pressure is detected as the output voltage Eo by the gauge 47 as described. The output voltage Eo is amplified by an amplifier 48 and, then, applied to a display device 49 which provides the information such as the number of breaths per unit time, respiration air volume and the volume of tidal air of the patient. Further, an alarm buzzer 50 and a recorder 51 are connected to the display device 49. The alarm buzzer 50 alarms against abnormal pressures inside the trachea of the patient and the recorder 51 serves to record the information provided by the display device. The observation system thus constructed permits observing rapidly and accurately the respiration state of the patient.

As described in detail, the heat and moisture exchanging device for respiration according to this invention is featured in that the heat and moisture exchange body is prepared by superposing a plurality of metal meshes of a high heat conductivity and is disposed substantially perpendicular to the respiratory air passage. The effect of the heat and moisture exchange body can be increased if it is prepared by superposing the metal meshes and moisture absorptive heat insulating sheets in combination. The heat and moisture exchange body disposed perpendicular to the respiratory air passage permits markedly sharpening the temperature gradient across the heat exchange body, compared with a prior art in which the heat and moisture exchange body made of aluminum foil is disposed parallel with the air passage. Thus, "the perpendicular type" heat and moisture exchange body is far more efficient in recoveries of heat and moisture than the "parallel type" one. Specifically, the former permits reducing its dead space to about one-fourth of that of the latter for recovering the same amounts of heat and moisture. This is very much advantageous in not only the manufacturing cost saving but also the handling of the device.

Another feature of this invention is that the heat and moisture exchanging device can be equipped with a system for observing the respiration state of the patient. Particularly, the differential pressure gauge constituting a part of the observation system is constructed such that the diaphragm 36 serves to protect the electrode 31. Accordingly, even where humid gas, sterilization gas or other corrosive gas is introduced into the differential pressure gauge, it suffices to make the outer surface alone of the diaphragm corrosion resistant.

Incidentally, necessary electronic circuit can be incorporated inside the diaphragms 36 for manufacturing the differential pressure gauge in place of the arrangement described. Also, various types of differential pressure gauge utilizing the inlet and outlet pressures can be connected to the heat and moisture exchanging device.

What is claimed is:

1. A heat and moisture exchange device for respiration comprising a housing having an inlet adapted for detachable connection to a trachael cannula and an outlet adapted for detachable connection to a tube for passing respiratory air, permeable heat and moisture exchange layers disposed between said inlet and said outlet substantially normal to the axis of passage of respiratory air between said inlet and outlet, a drainage tube having one end extending through said housing adjacent said layers with the other free end being open for flow of fluid out of said tube, said one end of said tube opening into contact with said permeable layers permitting liquid accumulated by said layers during operation of said device to be drained out of the housing, holes through the walls of said housing adjacent the inlet and outlet thereof and a differential pressure gauge connected by tubes to said holes to permit said gauge to measure the pressure difference between said inlet and said outlet.

2. A heat and moisture exchange for respiration comprising a housing having an inlet adapted for detachable connection to a tracheal cannula and an outlet adapted for detachable connection to a tube for passing respiratory air, permeable heat and moisture exchange layers disposed between said inlet and said outlet substantially normal to the axis of passage of respiratory air between said inlet and outlet and a drainage tube having one end extending through said housing adjacent said layers with the other free end having a plurality of openings in its wall for flow of fluid out of said tube, said one end of said tube opening into contact with said permeable layers, said drainage tube being loaded with fibrous material capable of conveying through the tube by capillary action liquid accumulated by said layers during operation of said device to drain the liquid out of said housing.

3. The device of claim 1 wherein the differential pressure gauge comprises a pair of electrically conducting diaphragms so flexible as to be readily deformable in response to pressure differences between said inlet and outlet, a pair of electrodes facing said diaphragms forming a pair of electrical capacitors, a pair of lids covering said pair of electrical capacitors, a hole in each lid, one lid hole being connected to said tube connected to said housing inlet and the other lid hole being connected to said tube connected to said housing outlet and an electric circuit generating an output signal representing the difference in capacitance between said capacitors.

4. The device of claim 3 further having means for amplifying said output signal, means for visually displaying said signal in terms of number of breaths per unit time, respiration air volume and volume of tidal air and means for recording said signal in said terms.

* * * * *